United States Patent [19]

Caputo et al.

[11] Patent Number: 5,244,629
[45] Date of Patent: * Sep. 14, 1993

[54] PLASMA STERILIZING PROCESS WITH PULSED ANTIMICROBIAL AGENT PRETREATMENT

[76] Inventors: Ross A. Caputo, 6533 Saddle Ridge La., Long Grove, Ill. 60047; Kern A. Moulton, 2221 Pyramid St., Livermore, Calif. 94550; Bryant A. Campbell, deceased, late of Los Gatos, Calif.; by Louise A. Campbell, legal representative, 107 Verona Ct., Los Gatos, Calif. 95030

[*] Notice: The portion of the term of this patent subsequent to Jan. 28, 2009 has been disclaimed.

[21] Appl. No.: 749,041

[22] Filed: Aug. 27, 1991

Related U.S. Application Data

[63] Continuation-in-part of Ser. No. 576,235, Aug. 31, 1990, Pat. No. 5,084,239.

[51] Int. Cl.$^5$ .......................... A61L 2/14; A61L 2/20
[52] U.S. Cl. ....................................... 422/22; 422/23; 422/28; 422/906; 422/907; 250/455.11
[58] Field of Search ................................. 422/22-23, 422/28, 906-907; 250/455.1

[56] References Cited

U.S. PATENT DOCUMENTS

| | | | |
|---|---|---|---|
| 3,383,163 | 5/1968 | Menashi | 422/23 |
| 3,410,776 | 11/1968 | Bersin | 422/186.29 |
| 3,428,548 | 2/1969 | Hollahan | 422/186.05 |
| 3,704,096 | 11/1972 | Verses et al. | 436/1 |
| 3,737,608 | 6/1973 | Nago et al. | 422/21 |
| 3,851,436 | 12/1974 | Fraser et al. | 53/434 |
| 3,948,601 | 4/1976 | Fraser et al. | 422/23 |
| 4,065,369 | 12/1977 | Ogawa et al. | 204/164 |
| 4,123,663 | 10/1978 | Horiike | 422/186.05 |
| 4,138,306 | 2/1979 | Niwa | 156/345 |
| 4,151,034 | 4/1979 | Yamamoto | 156/345 |
| 4,160,690 | 7/1979 | Shibagaki | 156/643 |
| 4,169,123 | 9/1979 | Moore et al. | 422/29 |
| 4,169,124 | 9/1979 | Forstrom et al. | 422/33 |
| 4,207,286 | 6/1980 | Boucher | 422/21 |
| 4,230,663 | 10/1980 | Forstrom et al. | 422/33 |
| 4,289,728 | 9/1981 | Peel et al. | 422/24 |
| 4,321,232 | 3/1982 | Bithell | 464/146 |
| 4,348,357 | 9/1982 | Bithell | 422/22 |
| 4,366,125 | 12/1982 | Kodera et al. | 422/295 |

(List continued on next page.)

FOREIGN PATENT DOCUMENTS 58-87825 5/1983 Japan.
2214081 1/1989 United Kingdom.

OTHER PUBLICATIONS

Hallohan et al., "Analytical Applications of Electrodelessly Discharged Gases" Chemical Instrumental, Journal of Chem. Education, 43:A401–A416.
Hallohan et al., "Research with Electrodelessly Discharged Gases," Chemical Instrument, 43:A497–A512.
Hallohan et al., "Chem. Education Letters," Journal of Chem. Education 43:392–393.

(List continued on next page.)

Primary Examiner—Lyle A. Alexander

[57] ABSTRACT

A process for plasma sterilization including exposing an article in a sterilizing chamber to at least one combination sterilizing cycle. Each combination sterilizing cycle includes a pulsed treatment with gaseous antimicrobial agent, removal of the gaseous antimicrobial agent, and a plasma treatment. The pulsed treatment includes one or more pulse-vacuum cycles, each pulse-vacuum cycle includes the steps of evacuating the sterilizing chamber and exposing the article to the gaseous antimicrobial agent with a predetermined pressure profile during a predetermined time. The gaseous antimicrobial agent is preferably carried in a gas mixture with a nonreactive carrier gas. In one embodiment, the predetermined pressure is pulsed. In another embodiment, it is ramped. After the pulsed treatment, the antimicrobial agent is removed by evacuating the sterilizing chamber. The plasma treatment includes exposing the article to a plasma having essentially uncharged, highly reactive free radicals and atoms.

18 Claims, 3 Drawing Sheets

U.S. PATENT DOCUMENTS

| | | | |
|---|---|---|---|
| 4,437,567 | 3/1984 | Jeng | 206/210 |
| 4,643,876 | 2/1987 | Jacobs et al. | 422/23 |
| 4,756,882 | 7/1988 | Jacob | 422/23 |
| 4,801,427 | 1/1989 | Jacob | 422/21 |
| 4,818,488 | 4/1989 | Jacob | 422/21 |
| 4,898,715 | 2/1990 | Jacob | 422/22 |
| 4,917,586 | 4/1990 | Jacob | 422/23 |
| 4,931,261 | 6/1990 | Jacob | 422/292 |
| 4,943,417 | 6/1990 | Jacob | 422/21 |
| 4,976,920 | 12/1990 | Jacob | 422/22 |
| 5,115,166 | 5/1992 | Campbell et al. | 422/23 |
| 5,178,829 | 1/1993 | Moulton et al. | 422/23 |

OTHER PUBLICATIONS

Hallohan et al., "Techniques and Applications of Plasma Chemistry," v-v11, 229-253.

Rudder et al., "Remote Plasma-Enhanced Chemical-Vapor Deposition of Epitaxial Ge Films," J. Appl. Phys., 60(1):3522.

Leaper et al., "Influence of Temperature on the Synergistic Sporicidal Effect of Peracetic Acid Plus Hydrogen Peroxide on *Bacillus Subtilis*" SA22 (NCA 72-52), Food Microbiology, 1:199-203, 1984.

Leaper et al., "A Note on the Effect of Storage on the Chemical Resistance of Spores of *Bacillus Subtilis* SA22 and *Bacillus Subtilis* Glogigii B17," J. Applied Biology 64:183-186, 1988.

Leaper et al., "Synergistic Killing of Spores of *Bacillus Subtilis* by Peracetic Acid and Alcohol," J. Food Technology, 19:355-360, 1984.

Leaper et al., "Comparison of the Resistance to Hydrogen Peroxide of Wet and Dry Spores of *Bacillus Subtilis* SA222," J. Food Technology, 19:695-702, 1984.

PLASMA STERILIZING PROCESS WITH PULSED ANTIMICROBIAL AGENT PRETREATMENT

This is a continuation in part of U.S. application Ser. No. 07/576,235, filed Aug. 31, 1990, now U.S. Pat. No. 4,084,239.

FIELD OF THE INVENTION

This invention relates to a plasma sterilization process comprising pulsed treatment with a gaseous or vaporized antimicrobial agent such as hydrogen peroxide or a peracid to kill microorganisms and spores on the article. In particular, this invention relates to exposing an article to be sterilized to a plurality of treatment cycles, each cycle including cyclic pulses of a gaseous or vaporized antimicrobial agent at one pressure, followed by pressure reduction to a lower pressure. The article is then exposed to a gas plasma.

BACKGROUND OF THE INVENTION

A variety of gas sterilization methods has been investigated in the past. Methods using ethylene oxide and other disinfecting gases are used for sterilizing a wide range of medical products from pharmaceutical preparations to surgical instruments. Irradiation alone or together with disinfecting gases has also been investigated, as summarized by Russell, A. THE DESTRUCTION OF BACTERIAL SPORES. New York: Academic Press (1982).

A sterilizing method must effectively kill all organisms, including spores, without damage to the article or goods being sterilized. However, many disinfecting gases which meet these criteria, such as ethylene oxide, and irradiation methods have been recognized to expose workers and the environment to safety hazards. States and Federal legislation are severely restricting the amount of hazardous gases such as ethylene oxide (a carcinogen) in the working environment, or the use of any system or method which produces toxic residues or exhaust products. This is presenting a major crisis in hospitals and other areas of the health industry.

DESCRIPTION OF THE PRIOR ART

Sterilizing plasmas have been generated with a wide variety of gases: argon, helium or xenon (U.S. Pat. No. 3,851,436); argon, nitrogen, oxygen, helium or xenon (U.S. Pat. No. 3,948,601); glutaraldehyde (U.S. Pat. No. 4,207,286); oxygen (U.S. Pat. No. 4,321,232); oxygen, nitrogen, helium, argon or Freon with pulsed pressure (U.S. Pat. No. 4,348,357); and hydrogen peroxide (U.S. Pat. Nos. 4,643,876 and 4,756,882). Sterilizing with ozone and singlet oxygen generated in a RF electric force field is described by U.S. Pat. No. 4,640,782. The plasma treatment found necessary to kill resistant spores has proven too severe for many packaging materials.

Typical prior art plasma sterilizing systems having a combination plasma generating and sterilizing chamber are exemplified by U.S. Pat. No. 4,643,876, for example. In these systems, the plasma is generated from hydrogen peroxide vapor and residue, and the article being sterilized is directly exposed to the plasma inducing electromagnetic field. The in situ generation of the ions and free radicals in the vicinity of the article surface is considered to be a critical part of the static process. Antimicrobial hydrogen peroxide pretreatment has been combined with exposure of the article to the electromagnetic plasma generating environment to remove any remaining hydrogen peroxide residues. The process is static, that is, the plasma is generated in the volume of gas initially in the closed chamber, and the articles are not exposed to plasma generated from a mixture of hydrogen, oxygen and inert gases, as in the process of this invention. These systems tend to rapidly decompose plastic and cellulose containing packages because of the strong oxidizing properties of the ions and free radicals in the elevated temperatures of the process. Limiting the process time to prevent package destruction also produces an incomplete spore kill rate.

Plasma gas sterilizer systems described in U.S. Pat. Nos. 3,851,436 and 3,948,601 comprise separate plasma RF generation chambers and sterilizing chambers. A gas plasma produced in the plasma generating chamber with argon, helium, nitrogen, oxygen or xenon is passed into a separate sterilization vacuum chamber containing the articles to be sterilized. These systems are not adequate for sterilizing contents of cellulose containing packages because the oxidizing plasma products degrade the packaging materials. They are not capable of producing satisfactory sterilization rate without package damage.

Non-plasma gas sterilization procedures have been described using ozone (U.S. Pat. No. 3,704,096) and hydrogen peroxide (U.S. Pat. Nos. 4,169,123, 4,169,124, 4,230,663, 4,289,728, 4,366,125, 4,437,567 and 4,643,876). However, these procedures are not entirely effective or leave toxic residues on the articles being sterilized.

Peracid sterilization processes have been disclosed in East German Patent Application Serial No. 268,396, EPO Patent Application Publication No. 109,352 A1, and U.K. Patent 2,214,081, for example. The sporicidal activities of peracetic acid, alone and in combination with other compounds including ethanol and hydrogen peroxide are disclosed by Leaper, S., *Food Microbiology.* 1:199-203 (1984); Leaper, S. et al, *J.Applied Biol.* 64:183-186 (1988); Leaper, S., *J.Food Technology.* 19:355-360 (1984); and Leaper, S., *J.Food Technology.* 19:695-702 (1984). These methods are not effective to sterilize the contents of packages containing cellulose and other materials which are reactive with peracid species.

The above apparatus and methods do not achieve complete sterilization for many types of articles requiring sterilization, and most produce damage to articles and packaging in the course of producing high sterilization rates. As a result, they do not achieve the necessary goal of providing an all purpose, effective sterilizing system and process.

Accordingly, one object of the present invention is to provide an efficient process which achieves complete sterilization with all types of articles used in the health care environment, including metallic articles and articles contained in porous sterilization packaging including cellulosic materials.

It is another object of the present invention to provide a low pressure, low temperature sterilization process which is effective for sterilizing packaged articles without destroying the integrity of the packages.

SUMMARY OF THE INVENTION

The process of this invention for sterilization includes exposing an article in a sterilizing chamber to at least one combination sterilizing cycle. Each sterilizing cycle is comprised of a pulsed treatment with gaseous antimicrobial agent, removal of the gaseous antimicrobial agent, and a plasma treatment. The pulsed treatment comprises one or more pulse-vacuum cycles, each pulse-vacuum cycle comprising the steps of evacuating the sterilizing chamber and exposing the article to the gaseous antimicrobial agent for a predetermined duration. After the pulsed treatment, the antimicrobial agent is removed by evacuating the sterilizing chamber. The plasma treatment comprises exposing the article to a stream of plasma having essentially uncharged, highly reactive free radicals which are oxidizing or reducing agents. The plasma is generated in a separate plasma generating chamber and is supplied to sterilize the article in the sterilization chamber. The pulsed treatment and the plasma treatment follow a predetermined order in each combination sterilizing cycle.

According to one aspect of the invention, the antimicrobial agent is preferably selected from the group consisting of hydrogen peroxide, a peracid antimicrobial agent, and mixtures thereof, the peracid antimicrobial agent being selected from the group consisting of saturated and unsaturated peralkanoic acids having from 1 to 8 carbon atoms and halogenated derivatives thereof.

According to another aspect of the invention, the pressure of the gaseous antimicrobial agent is ramped up (i.e. monotonically increased) during the predetermined duration.

According to another aspect of the invention, the gaseous antimicrobial agent is carried in a gaseous mixture with a nonreactive carrier gas.

According to another aspect of the invention, the gaseous mixture is maintained at substantially a maximum concentration supported by the temperature maintained in the sterilization chamber.

According to yet another aspect of the invention, the gaseous antimicrobial agent in the gaseous mixture has a partial pressure substantially at its saturation vapor pressure supported by the temperature maintained in the sterilization chamber.

According to another aspect of the invention, water vapor is mixed with the gaseous antimicrobial agent to enhance its sterilizing action.

This combination sterilizing cycle treatment process is particularly suitable for sterilizing a porous article or an article enclosed in a porous container, the container being surrounded by the gas plasma during the treatment, even when the porous container comprises a carbohydrate composition.

DETAILED DESCRIPTION OF THE INVENTION

Hospitals originally relied on disinfectants and steam autoclaves for sterilizing implements. In more recent years, ethylene oxide gas sterilization has made possible the sterilization of packaged articles, drugs and medical supplies, and hospital systems are highly dependent upon these procedures. However, ethylene oxide is now known to be a dangerous carcinogen, and a number of new state laws protecting worker safety and the environment are precluding further use of ethylene oxide sterilizers in hospital environments.

Numerous gas plasma sterilizers using a wide variety of gases have been described in the literature. A few have been commercially produced. One system described in U.S. Pat. No. 4,643,876, for example, pretreats the article to be sterilized with hydrogen peroxide before it is placed in the electromagnetic field producing the plasma. It relies on the presence of the hydrogen peroxide residue in the electromagnetic field as a source of the plasma products and the direct exposure the hydrogen peroxide residue to the electromagnetic field to eliminate hydrogen peroxide residues. This system is suitable only for sterilizing non-metallic articles because of the heating of metallic articles and the destabilizing effect of metallic articles in plasma generating electromagnetic fields. However, even with hydrogen peroxide pretreatment, complete sterilization is not achieved without severe degradation of the packaging materials.

Peracids such as peracetic acid are well known as sterilizing agents in situations where their residues can be tolerated or easily removed and where adequate exposure time is allowed. However, peracid vapors are also known to be ineffective for sterilizing goods packaged in the conventional cellulosic sterile packages used in the health care field.

This invention is based on the discovery that pulsed antimicrobial agent pretreatment of both packaged and unpackaged articles, followed by exposure of the articles to sterilizing gas plasmas, reliably and more efficiently kills resistant spores at conditions which are not destructive to packaging materials. The exposure to the gas plasma in a sterilizing chamber separate from the plasma generating system protects the packaging and plastic components and permits the sterilization of metallic articles.

The term "sterilization" connotes a process by which all viable forms of microorganisms are destroyed or removed from an object. Since microorganisms die according to first order chemical kinetics, it is customary to define sterility in terms of "probability of survivors". The practical goal of a sterilization process is therefore measured as a probability (e.g., $10^{-3}$, $10^{-6}$, $10^{-12}$), the probability indicating the lethal effect of a particular sterilizing dose or regimen. It is usual to assume increased time of exposure to a set of sterilizing conditions will decrease the probability of survivors accordingly. Doubling the sterilizing time of identical conditions would result in a doubling of the exponent of the probability term, for example $10^{-6}$ would become $10^{-12}$.

The term "pretreatment" is used herein to define that at least one pulsed treatment of the article being sterilized with antimicrobial agent is followed by treatment with gaseous plasma products. The "pretreatment" with antimicrobial agent can follow one or more earlier plasma treatments and can be followed by one or more plasma treatments. Repetitions of the pulsed treatment and plasma gas treatment cycle any number of times can be used until total killing of spores with even the most resistant articles is achieved. The combination of peroxide and/or peracid antimicrobial agent and plasma gas treatments is synergistic in achieving a spore kill rate which exceeds the killing rate which can be achieved by use of hydrogen peroxide or peracid alone, or plasma gases alone, while preserving the integrity of packaging materials. The residues are also entirely eliminated by the plasma gases and vacuum.

The pulsed treatment comprises one or more pulse-vacuum cycles. Each pulse-vacuum cycle preferably begins by evacuating the sterilization chamber. This is followed by exposing the article to be sterilized in the sterilization chamber to gaseous antimicrobial agent at a predetermined pressure for a predetermined period. If the antimicrobial agent exists in a liquid state at room temperature, it is first vaporized at an elevated temperature not exceeding the operating temperature of the sterilization chamber. For considerations of stability, ease of transport, and higher operating pressures, the vaporized antimicrobial agent may be carried in a mixture with a nonreactive carrier gas such as an inert or noble gas.

According to one aspect of the invention, water vapor is also mixed with the gaseous antimicrobial agent to enhance its sterilizing action. It has been discovered that with vaporized peracetic acid as the antimicrobial agent, a relative humidity of 20-100% further enhances the effectiveness.

Preferably, the pressure is such that the antimicrobial agent is maintained at substantially the maximum concentration supported by the temperature in the sterilization chamber without occurrence of condensation. Thus the partial pressure of the antimicrobial agent is preferably near the saturation vapor pressure of the antimicrobial agent for the temperature in the sterilization chamber.

In one embodiment, the pressure of the antimicrobial agent and the carrier gas introduced into the sterilization chamber is pulsed. Preferably the pressure pulses are in the range of from 4 to 50 torr. This helps to replenish antimicrobial agent consumed by reaction with the article. It also helps to drive the antimicrobial agent into packaging barrier or to diffuse into long lumens of medical devices, such as flexible endoscopes or hypodermic needles.

In another embodiment, the pressure is ramped up (i.e. monotonically increased) during the predetermined exposure period. In general pulsing helps to drive the antimicrobial agent into the article and increasing the pressure with time helps to replenish spent agent. Other pressure profiles having a combination of pulsing and ramping are also possible.

The term "peracid" as used herein, is defined to include well known peracid antimicrobial agents such as saturated and unsaturated peralkanoic acids including peraralkanoic acids having from 1 to 8 carbon atoms and halogenated derivatives thereof. Examples of suitable peracids include known peracetic acid, halogenated peracetic acids, performic acid, perpropionic acid, halogenated perpropionic acids, perbutanoic acid and its halogen derivatives, perisovaleric acid and its halogen derivatives, percapronic acid and its halogen derivatives, percrotonic acid, monopersuccinic acid, monoperglutaric acid, and perbenzoic acid, for example. The halogenated peracids contain one or more chloro, bromo, iodo or fluoro groups. The preferred peracids are sufficiently volatile to form an effective sporicidal vapor concentration at temperatures less than 80° C.

It is to be understood that the operating temperature of the present process is determined by the characteristics of the articles being sterilized, not by temperature limitations of the sterilization process. Many medical articles to be sterilized will not withstand temperature over 60° C., while other articles such as metallic surgical instruments are more efficiently sterilized at higher temperatures.

In the pulsed treatment using hydrogen peroxide, the article is contacted with hydrogen peroxide vapors produced by completely evaporating 1 to 10% (wt/wt) hydrogen peroxide solution and preferably from 2 to 8% (wt/wt) hydrogen peroxide solution. The optimal vapor pretreatment involves contacting the article to be sterilized with hydrogen peroxide vapor in the sterilizing chamber. A total pulsed contact time of from 5 to 15 minutes is usually sufficient to insure contact of the entire surface of a packaged article with the hydrogen peroxide vapor.

In the pulsed treatment with peracid, peracid treatment is effected by contact of the article with antimicrobial concentrations of the peracid vapor. Preferably, the pulsed peracid pretreatment is carried out by exposing the article to be sterilized to peracid vapor produced by completely evaporating from 1 to 35% (wt/wt) peracid solution and preferably from 6 to 12% (wt/wt) peracid solution for a time sufficient to permit contact of the vapor with all surfaces of the article being sterilized, packaged or unpackaged. The total pulsed contact exposure time is preferably from 5 to 15 minutes with packaged articles. For temperature-sensitive articles, the peracid exposure can be carried out at a temperature of from 20° to 80° C. and preferably from 40° to 60° C. Treatment at higher temperatures is possible for articles being sterilized that can tolerate them.

Some peracids in certain concentrations are explosive at elevated temperatures. For this reason, peracetic acid is usually transported and stored in aqueous solutions having less than 35 wt. % peracetic acid. The peracetic acid solution is easily vaporized, and effective treatment of articles at room temperature, according to this invention, can be achieved by exposing the articles to peracetic acid vapors at partial pressures in the range of from 1 to 18 torr. The lower pressure limit is the lower range limit of the effective concentration of the peracetic acid, and the upper limit is the saturation vapor pressure at room temperature. If the article to be sterilized can tolerate higher temperatures, then the pressure range will change accordingly.

After the pulsed treatment, the mixture gas carrying the antimicrobial agent is removed by evacuating the sterilization chamber. Plasma gas is then introduced into the sterilization chamber to sterilize the article inside.

The particular pulse-vacuum sequence order can be reversed as desired during successive repetitions of the pulsed treatment and plasma treatment cycle.

In the preferred process of this invention, the pulsed antimicrobial agent pretreatment is carried out with vapor introduced into the sterilizing chamber, and the article is pretreated with the peracid prior to exposing the article to the plasma. Suitable plasma sterilizing systems for carrying out the process of this invention are described in copending, commonly assigned U.S.

Pat. Nos. 5,115,166 and 5,178,829, the entire contents of which are hereby incorporated by reference.

The process of this invention uses a plasma made from gas mixtures containing argon, helium and/or nitrogen; and oxygen and/or hydrogen, optionally containing inert gases and carbon dioxide. Nitrogen is not preferred because it can form toxic residues. The exhaust gas products fully satisfy current environmental and worker safety concerns, the products of the plasma being almost entirely water vapor, carbon dioxide and non-toxic gases normally found in the atmosphere.

The term "plasma" as used herein is defined to include any portion of the gas or vapors which contain electrons, ions, free radicals, dissociated and/or excited atoms or molecules produced as a result of the applied electric or electromagnetic field including any accompanying radiation which might be produced. The electromagnetic field can cover a broad frequency range, and can be produced by a magnetron, klystron or RF coil. For purposes of clarity of presentation and not by way of limitation, the description hereinafter describes the use of a magnetron as the electromagnetic field source, and the use of all other suitable sources of the electromagnetic field required for plasma production are intended to be included in this invention, including without limitation, magnetrons, klystron tubes, RF coils, and the like.

Generally, a plasma is generated with an initial large component of high energy ions and ultraviolet (UV) emission as a matter of course. As the plasma is transported down stream and out of the plasma generating energy field, the charged particles recombine by collision with container surfaces to uncharged energized free radicals, atoms and molecules.

An important feature of the present invention is to avoid the use of plasma having a large component of ions and ultraviolet emissions to effect sterilization. Instead, uncharged species of oxidizing or reducing agents, made highly reactive by activation with the plasma, are used to effect sterilization by a chemical process.

The apparatus disclosed herein is capable of producing plasma having uncharged, highly reactive species. For example, in the plasma generating chamber, oxygen is energized by microwave radiation and forms a plasma having an initial high concentration of ions and ultraviolet emissions. These are not allowed into the sterilization chamber as they tend to be strongly corrosive on the article to be sterilized, or the packaging. The UV emissions are localized in the plasma generating chamber and are attenuated by the restriction means and the plasma distribution means before they reach the sterilizing chamber. Similarly, as high energy ions hit the restrictive means and the internal wall of the plasma distribution means, they recombine with free electrons to revert to highly reactive uncharged atoms and radicals. By the time the plasma enters the sterilizing chamber, the plasma's downstream products consist essentially of energized and highly reactive uncharged free radicals and electronically excited uncharged atoms and molecules.

Typically, a microwave source is used to generate the plasma. It is channeled by a waveguide to form a highly confined EM field zone. Little of that field can spread to the sterilizing chamber. Thus, production of high energy ions and UV is only possible in the field region of the plasma generating chamber and not outside of it. Also, there is no EM field to cause non-uniformity in the sterilizing chamber. The restriction means of Applicants' apparatus, apart from obstructing the passage of UV and ions as noted above, further helps to make plasma generation outside the plasma generating chamber less favorable. The restriction means maintains an optimal gas pressure in the plasma generating chamber for generating plasma. Once the gas exits via the restriction means, the pressure drops to make generation impossible under normal conditions even if the EM field of the microwave source extended into this region. Thus, UV and ions can only be generated in the plasma generating chamber; once outside, they are allowed to dissipate to form a downstream plasma consisting essentially of energized, highly reactive uncharged free radicals.

Under these conditions, effective sterilization is effected without significant deterioration of packaging materials in which articles to be sterilized may be placed.

Figure 1:
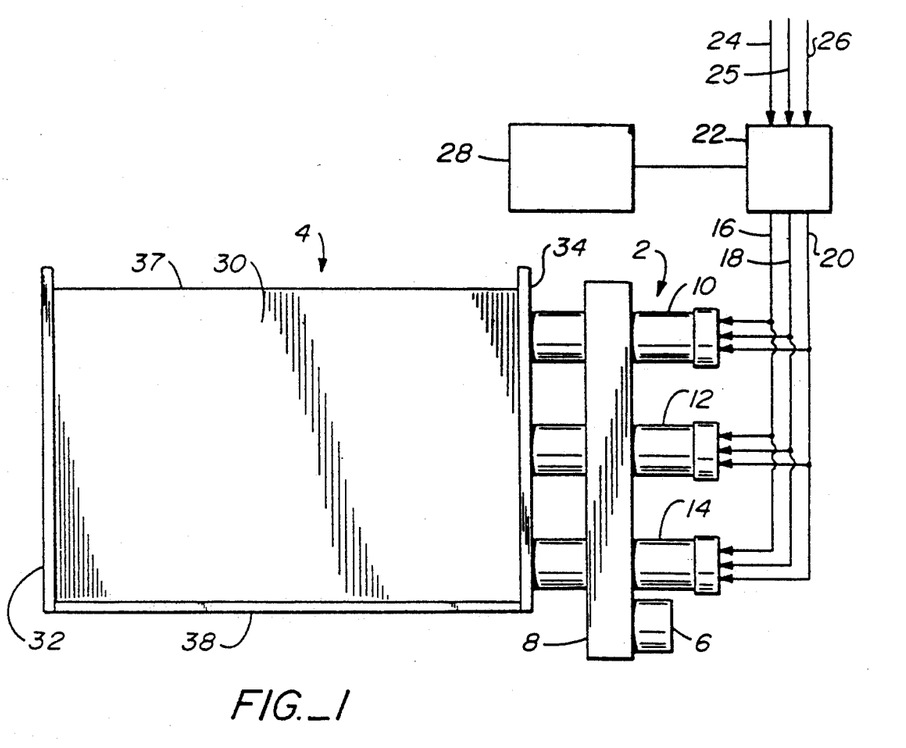
FIG. 1 is a top view of a plasma sterilizer of this invention.
Figure 2:
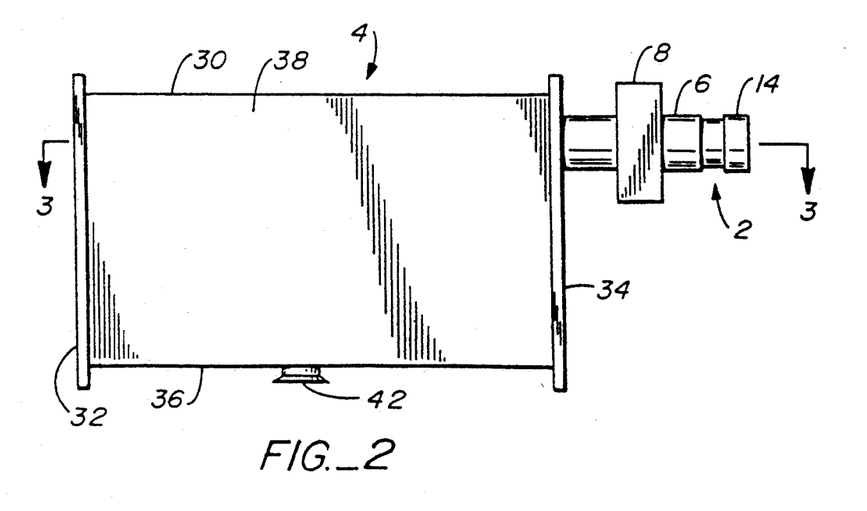
FIG. 2 is a front view of the plasma sterilizer embodiment of FIG. 1.

One suitable apparatus is shown in FIG. 1. FIG. 1 is a top view and FIG. 2 is a front view of a single waveguide plasma sterilizer embodiment of this invention. The plasma sterilizer has a plasma generator 2 and a sterilizing chamber 4. The plasma generator 2 comprises an electromagnetic field generator such as a magnetron 6 and a waveguide 8 which directs the electromagnetic field. The plasma source gases are directed into plasma generating and delivering tubes 10, 12, and 14 by feeder tubes from gas delivery tubes 16, 18 and 20 leading from the control valve complex 22. Individual gases are fed from the pressured gas sources (not shown) by inlet lines 24, 25 and 26. The operation of the control valves in valve complex 22 is controlled by the central processing unit (CPU) 28 by standard procedures. The control valves and CPU can be any of the conventional, standard devices used for gas flow control in plasma generating equipment.

The sterilizing chamber 4 comprises top plate 30, side plates 32 and 34, bottom plate 36, back plate 37 and front sealing door 38 through which articles or materials to be sterilized are placed in the chamber. The plates are attached together in a sealed relationship to form a vacuum chamber, such as by welding. The door 38 is secured in a sealed relationship with the sterilizing chamber. It is hinged at the top, side or bottom with conventional hinge pins (structure not shown) to swing against abutting surfaces and an O-ring seal 40 (FIG. 3) of the side, top and bottom plates, where the pressure difference between the internal chamber vacuum pressure and the surrounding atmospheric pressure holds it tightly in place.

The plates and door can be made of any material having the strength required to withstand the external atmospheric pressure when the chamber is evacuated. Stainless steel or aluminum plates and door are preferred. The internal surface material of the chamber is critical and greatly affects the number of killing species available in the chamber. An optimum material is an inert polymer such as polytetrafluoroethylene (Teflon). An alternate material is pure (98%) aluminum which can be applied either as a liner or as a flame-sprayed coating on all internal walls of the stainless steel chamber. Another alternate material is nickel.

Figure 4:
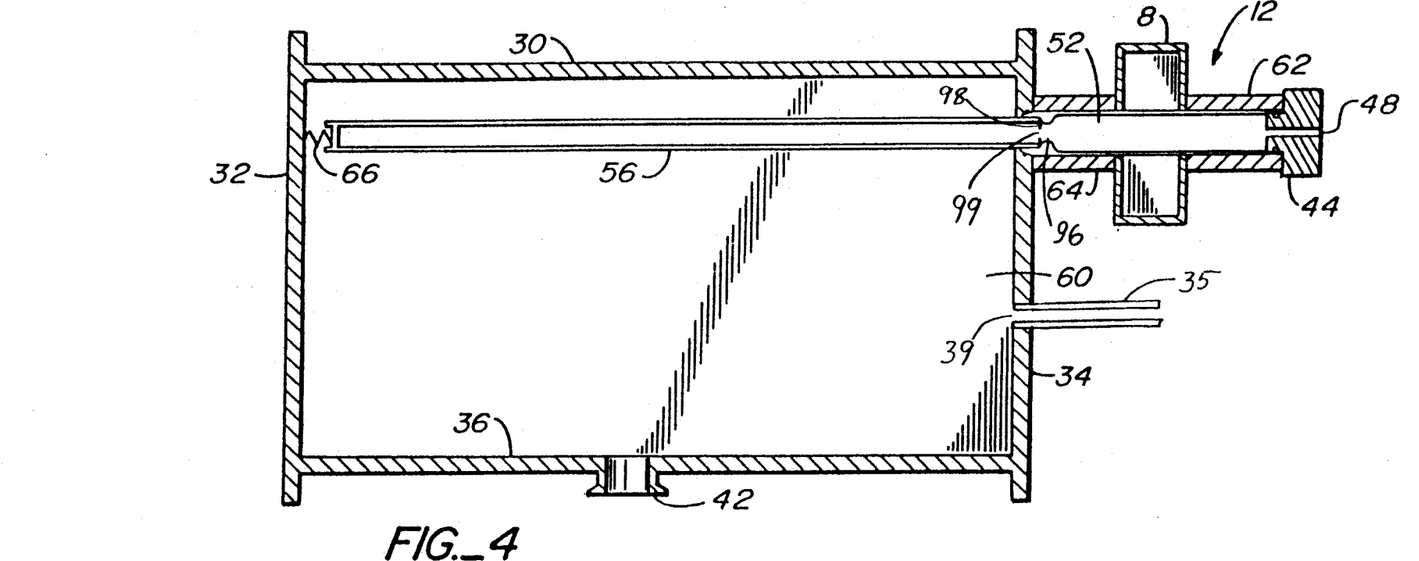
FIG. 4 is a cross-sectional view of the plasma sterilizer embodiment of FIG. 3, taken along the line 4—4.

Antimicrobial additives are added as a liquid or vapor through conduit 35 to inlet port 39 (FIG. 4). The gases are exhausted from the sterilizing chamber through exhaust outlet port 42 to a conventional vacuum pump system (not shown).

Figure 3:
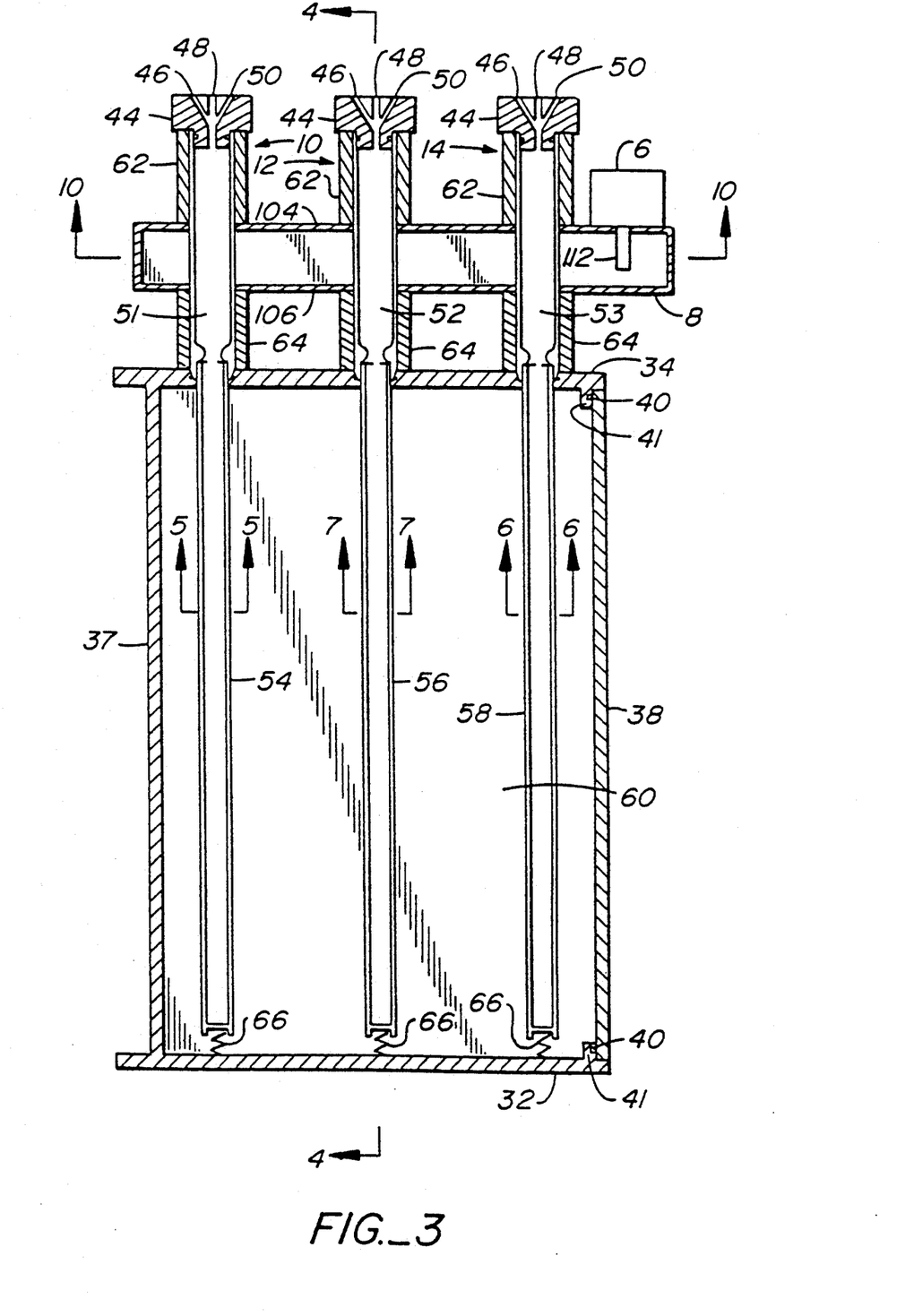
FIG. 3 is a cross-sectional view of the plasma sterilizer embodiment of FIG. 1 and FIG. 2, taken along the line 3—3 in FIG. 2.

FIG. 3 is a top cross-sectional view of the plasma sterilizer embodiment of FIG. 1 and FIG. 2, taken along the line 3—3 in FIG. 2. FIG. 4 is a side cross-sectional view of the plasma sterilizer embodiment of FIG. 1 and FIG. 3, taken along the line 4—4 in FIG. 3. Each of the plasma generators 10, 12 and 14 comprise an inlet cap 44 with gas inlet ports 46, 48 and 50 leading to a respective gas generator tube 51, 52 or 53 leading through the waveguide 8. In the waveguide 8, the gases are energized and convert in tubes 51, 52 and 53 to a plasma. The gas generator tube directs the plasma flow into the gas distribution tubes 54, 56 and 58 from which the plasma is fed into the sterilizing chamber 60. The gas generator tubes are enclosed in tubular metal cooling tubes 62 and 64. The caps 44 and the cooling tubes 62 and 64 are preferably provided with grooves or cooling fins (not shown) in a conventional manner to increase their efficiency in removing heat from gas generator tubes.

The distal end of tubes 51, 52 and 53 have increased thickness and forms a smooth surfaced venturi restriction 96 of reduced cross-sectional area. Cap 98 positioned on the proximal end of plasma distribution tube 56 has a preselected restrictive opening 99 of further reduced cross-sectional area. These restrictions are critical aspects of the preferred embodiment of this invention, creating a pressure difference between the low pressure plasma generating zone 87 and the vacuum pressure in the distribution tube 56 and sterilizing chamber 60.

The diameter of the restriction diameter 99 is selected to maintain a back pressure of from 0.3 to 10 torr, preferably from 1 to 6 torr and optimally from 5 to 6 torr in the plasma generating zone with a vacuum chamber pressure in the range of from 0.3 to 2 torr. This pressure provides optimum energy transfer from the electromagnetic field to the gases with gas mixtures containing oxygen; argon, helium and/or nitrogen; and/or hydrogen and is a major factor for the production of a high yield of plasma at a minimum temperature and with the minimum power requirement achieved with the device of this invention. For most operating parameters, the restriction 99 can have a diameter of from 4.82 to 8.00 mm and preferably from 6.28 to 6.54 mm. These dimensions may also vary if gas flows, vacuum system or the conductance of the gas distribution system changes.

The distal ends of the gas distribution tubes 54, 56 and 58 are supported by spring-biased end supports 66 mounted on sideplate 32.

The door 38 is held in sealing engagement by atmospheric pressure against the O-ring seal 40 mounted in the flange 41 extending from the side plates 32 and 34, and the top and bottom plates 30 and 36 (not shown). Optionally, additional conventional closure clamps or latches can be used to insure closure of the door before chamber evacuation is initiated.

Figure 5:
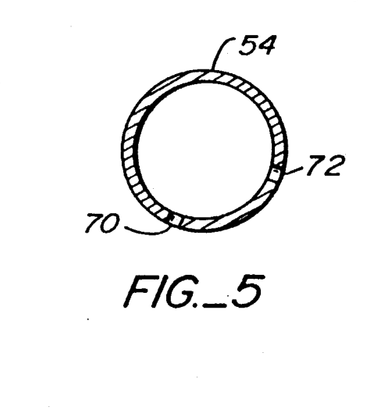
FIG. 5 is a cross-sectional view of tube 54 taken along line 5—5 in FIG. 3.
Figure 6:
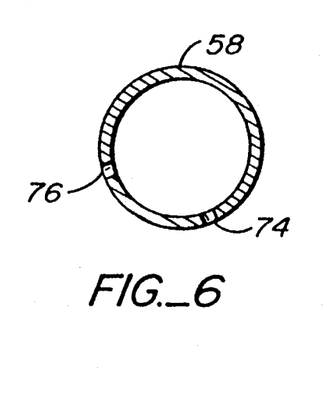
FIG. 6 is a cross-sectional view of tube 58 taken along line 6—6 in FIG. 3.
Figure 7:
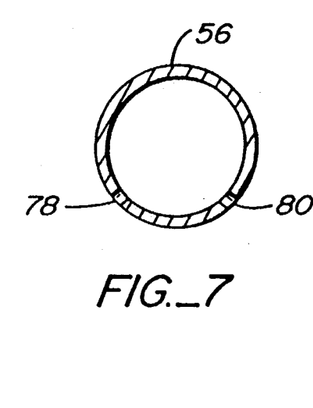
FIG. 7 is a cross-sectional view of tube 56 taken along line 7—7 in FIG. 3.

FIG. 5, FIG. 6 and FIG. 7 are cross-sectional views of gas distribution tubes 54, 58 and 56, respectively, showing angular positions of the gas distribution outlet ports. The outlet ports are positioned to provide plasma flow to all lower portions of the sterilizing chamber 60 where articles to be sterilized are placed. Tube 54 shown in FIG. 5 is placed adjacent back plate 37 and directs plasma gases downward and toward the lower center of the chamber through outlet ports 70 and 72, respectively. Tube 58 shown in FIG. 6 is placed adjacent the door 38 and directs plasma gases downward and toward the lower center of the chamber through outlet ports 74 and 76, respectively. Tube 56 shown in FIG. 7 is placed in the central portion of the chamber 60 and directs plasma gases laterally downward through outlet ports 78 and 80. The outlet ports shown for the distribution tubes are representative and can be changed to any other configuration which achieves optimal plasma distribution to the sterilizing zone or zones of the chamber. Although only one angular arrangement is shown, each tube can have more than one angular set of outlet ports, each having different angles, along the length of the tube, as desired. The choice of outlet port angles and locations should be selected in view of how the articles to be sterilized are to be placed in the chamber and the type of article to be sterilized.

The plasma is directed through a change of direction, preferably at least 90°, before discharging it into the sterilizing chamber. This prevents direct impingement of hot plasma onto the articles being sterilized. The gas distributors also allow ions to recombine by collisions with their surfaces and allow the UV radiation to dissipate.

The apparatus can be used to generate a sterilizing plasma from a mixture of oxygen; argon, helium, and/or nitrogen; and hydrogen, or with a mixture of air and hydrogen, supplemented by oxygen or nitrogen to give the desired ratios. The sterilization is carried out at a vacuum pressure of from 0.1 to 10 torr and preferably from 1 to 3 torr. Sterilization may be carried out at higher pressures provided steps are taken to ensure uniformity of gas flows and temperature throughout the chamber. The temperature in the sterilizing chamber is maintained below 80° C. and preferably from 38° to 60° C. for articles that can not tolerate high temperatures. Elevated temperatures may preferably be used with articles capable of withstanding them.

Following pulsed treatment with antimicrobial agent, the sterilizing chamber is evacuated to a pressure of less than 10 torr. The article is then exposed to a plasma generated from a gaseous mixture of argon, helium or nitrogen mixed with oxygen and/or hydrogen at temperatures of less than 80° C., a pressure of from 0.1 to 10 torr, and a treatment time of at least 5, and preferably from 10 to 15 minutes. For sterilizing packaged goods, the gas mixtures from which the plasma is generated can contain from 1 to 21 (v/v) % oxygen and from 1 to 20 (v/v) % hydrogen, the balance being argon, helium and/or nitrogen and optional small quantities of inert gases.

The gas mixtures producing plasmas for sterilizing packages preferably contain from 1 to 10% (v/v) oxygen and from 2 to 8% (v/v) hydrogen, and optimally contain from 2 to 8% (v/v) oxygen and from 3 to 7% (v/v) hydrogen. Packages are treated for at least 15 minutes and preferably from 1 to 5 hours.

One preferred embodiment of the process of this invention comprising the following steps, after placing the articles to be sterilized in the sterilizing chamber:

1. The sterilizing chamber is evacuated to a pressure of 0.1 torr, and an isolation valve between the vacuum pump and sterilizing chamber is closed.

2. A pulse of vaporized peracetic acid in a gaseous mixture with argon and/or water vapor as a carrier gas is admitted into the chamber. The peracetic acid vapor has a concentration of at least 2 mg/L peracetic acid. Alternatively, a pulse of vaporized hydrogen peroxide in a gaseous mixture with argon as a carrier gas is introduced into the chamber. The hydrogen peroxide vapor has a concentration of at least 2 mg/L hydrogen peroxide. If peracetic acid pretreatment is to be combined with hydrogen peroxide pretreatment, vaporized peracetic acid in a gaseous mixture with argon and/or water vapor as a carrier gas is admitted into the chamber. The peracetic acid vapor has a concentration of 2 mg/L peracetic acid.

The pulse of vaporized peracetic acid and/or hydrogen peroxide vapor exposure is continued for from 5 to 15 minutes.

3. The pressure in the sterilizing chamber is reduced to less than 2 torr for from 1 to 2 minutes.

4. Steps 2 and 3 are repeated 4 times, and the chamber is evacuated to 0.1 torr.

5. Process gases are admitted to the plasma chamber, preferably at a flow rate of up to 5 liters per minute, and optimally from 3 to 4 liters per minute.

6. The magnetron is energized to create the plasma, and the plasma products flow into the sterilizing chamber.

7. The plasma treatment is continued for from 5 to 30 minutes and preferably from 5 to 15 minutes.

8. The magnetron is deactivated and the process gas flow to the plasma chamber is terminated.

9. Steps 1-8 are repeated until sterilization is complete and all spores are killed. Hydrogen peroxide and peracetic acid treatments can be alternated so that the pretreatment is limited to either one for a particular cycle repetition.

10. The isolation valve between the pump and chamber is closed, and the chamber is vented to the atmosphere. The sterilizing chamber can be pumped down and partially vented to remove acidic vapors before being fully vented to the atmosphere.

The above method sterilizes effectively in less time than is required without the pulsed antimicrobial agent treatment, particularly for porous articles and articles enclosed in porous packages. Furthermore, it is effective for sterilizing all materials, while plasma and peracids, alone, have limited ability.

While the embodiments of the various aspects of the present invention that have been described are the preferred implementation, those skilled in the art will understand that variations thereof may also be possible. Therefore, the invention is entitled to protection within the scope of the appended claims.

It is claimed:

1. A process for plasma sterilization including exposing an article in a sterilizing chamber to at least one combination sterilizing cycle, each combination sterilizing cycle comprising:
   a pulsed treatment with gaseous antimicrobial agent, said pulsed treatment comprising one or more pulse-vacuum cycles, each pulse-vacuum cycle comprising the steps of evacuating the sterilizing chamber and exposing the article therein to gaseous antimicrobial agent for a predetermined duration;
   removing the antimicrobial agent after the pulsed treatment by evacuating the sterilization chamber; and
   a plasma treatment comprising exposing the article to a stream of plasma generated from gases consisting essentially of argon, helium, nitrogen, oxygen, hydrogen and mixtures thereof, said plasma being generated in a separate plasma generating chamber and being supplied to sterilize the article in the sterilization chamber.

2. The process of claim 1, wherein the pulsed treatment and the plasma treatment in each combination sterilizing cycle follow a predetermined order.

3. The process of claim 1, wherein the step of exposing the article to gaseous antimicrobial agent for a predetermined duration includes ramping the pressure of the gaseous antimicrobial agent.

4. The process of claim 1 wherein the antimicrobial agent is selected from the group consisting of hydrogen peroxide, a peracid antimicrobial agent, and mixtures thereof, the peracid antimicrobial agent being selected from the group consisting of saturated and unsaturated peralkanoic acids having from 1 to 8 carbon atoms and halogenated derivatives thereof.

5. The process of claim 4 wherein the peracid antimicrobial agent is peracetic acid.

6. The process of claim 4 wherein the antimicrobial agent is halogenated peracetic acid.

7. The process of claim 4 wherein the antimicrobial agent is hydrogen peroxide.

8. The process of claim 4 wherein the antimicrobial agent is a mixture of peracetic acid and hydrogen peroxide.

9. The process of claim 1, wherein the gaseous antimicrobial agent is carried in a gaseous mixture with a nonreactive carrier gas.

10. The process of claim 9, wherein the gaseous antimicrobial agent in the gaseous mixture has a partial pressure of from 4 to 50 torr, and the gaseous mixture with the antimicrobial agent is removed after the pulsed treatment by evacuating the sterilizing chamber to a pressure of less than 4 torr.

11. The process of claim 9, wherein the gaseous antimicrobial agent in the gaseous mixture in the sterilization chamber is maintained at a predetermined temperature and at partial pressures up to a maximum concentration of the antimicrobial agent supported by said predetermined temperature without the occurrence of condensation of the antimicrobial agent.

12. The process of claim 9 wherein the antimicrobial agent is selected from the group consisting of hydrogen peroxide, a peracid antimicrobial agent, and mixtures thereof, the peracid antimicrobial agent being selected from the group consisting of saturated and unsaturated peralkanoic acids having from 1 to 8 carbon atoms and halogenated derivatives thereof.

13. The process of claim 9 wherein the peracid antimicrobial agent is peracetic acid.

14. The process of claim 9 wherein the antimicrobial agent is halogenated peracetic acid.

15. The process of claim 9 wherein the antimicrobial agent is hydrogen peroxide.

16. The process of claim 9 wherein the antimicrobial agent is a mixture of peracetic acid and hydrogen peroxide.

17. The process of claim 9 wherein the gaseous mixture additionally includes water vapor.

18. A process for plasma sterilization including exposing an article in a sterilizing chamber to at least one combination sterilizing cycle, each combination sterilizing cycle comprising:
   an antimicrobial pretreatment by exposing the article in the sterilizing chamber to gaseous antimicrobial agent;
   removing the antimicrobial agent from the sterilization chamber; and
   exposing the article in the sterilization chamber to a stream of plasma generated from gases consisting essentially of argon, helium, nitrogen, oxygen, hydrogen and mixtures thereof, said plasma being generated in a separate plasma generating chamber.

* * * * *

UNITED STATES PATENT AND TRADEMARK OFFICE
CERTIFICATE OF CORRECTION

PATENT NO. : 5,244,629
DATED : SEPTEMBER 14, 1993
INVENTOR(S) : Caputo et al.

It is certified that error appears in the above-indentified patent and that said Letters Patent is hereby corrected as shown below:

On title page, item [73]  -- Assignee: Abtox, Inc., Pleasanton, Calif. --

On the title page,  -- Attorney, Agent or Firm: Majestic, Parsons, Siebert & Hsue --

Signed and Sealed this

Twenty-fifth Day of July, 1995

Attest:

BRUCE LEHMAN

*Attesting Officer*  *Commissioner of Patents and Trademarks*